(12) United States Patent
Montgomery

(10) Patent No.: US 6,322,773 B1
(45) Date of Patent: *Nov. 27, 2001

(54) TOOTH-BLEACHING COMPOSITIONS

(75) Inventor: R. Eric Montgomery, P.O. Box 487, 29 Fairview Rd., Monterey, MA (US) 01245

(73) Assignees: R. Eric Montgomery; Idex Dental Sciences, Inc., both of Monterey, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/374,172

(22) Filed: Aug. 13, 1999

Related U.S. Application Data

(63) Continuation of application No. 09/054,156, filed on Apr. 2, 1998, and a continuation of application No. 09/192,609, filed on Nov. 16, 1998, each is a division of application No. 08/719,569, filed on Sep. 25, 1996, now Pat. No. 5,922,307.
(60) Provisional application No. 60/004,258, filed on Sep. 25, 1995.

(51) Int. Cl.[7] .............................. A61K 7/20; A61C 15/00; B67D 5/52; B01F 15/02
(52) U.S. Cl. ............................ 424/53; 206/219; 206/221; 222/94; 222/137; 222/145.6; 366/136; 366/160.3; 433/215; 433/216
(58) Field of Search .......................... 424/53; 433/215, 433/216; 206/219, 220; 366/136, 176; 222/94, 137, 145.5

(56) References Cited

U.S. PATENT DOCUMENTS

| | | | |
|---|---|---|---|
| D. 315,496 * | 3/1991 | Pettengill ........................ D9/373 |
| 3,286,992 * | 11/1966 | Armeniades et al. ............... 259/4 |
| 3,664,638 * | 5/1972 | Grout et al. ....................... 259/4 |
| 4,408,893 * | 10/1983 | Rice ................................. 366/339 |
| 4,538,920 * | 9/1985 | Drake ............................... 366/177 |
| 4,632,568 * | 12/1986 | Emele et al. ..................... 366/337 |
| 4,687,663 * | 8/1987 | Schaeffer ......................... 424/53 |
| 4,767,026 * | 8/1988 | Keller et al. ..................... 222/137 |
| 4,941,751 * | 7/1990 | Muhlbauer ....................... 366/176 |
| 4,952,068 * | 8/1990 | Flint ................................. 366/337 |
| 4,964,539 * | 10/1990 | Mueller ............................ 222/94 |
| 4,988,500 * | 1/1991 | Hunter ............................. 424/53 |
| 5,020,694 * | 6/1991 | Pettengill ......................... 222/137 |
| 5,038,963 * | 8/1991 | Pettengill et al. ................ 222/145 |
| 5,059,417 * | 10/1991 | Williams et al. ................. 424/53 |
| 5,165,424 * | 11/1992 | Silverman ........................ 128/861 |
| 5,374,368 * | 12/1994 | Hauschild ......................... 252/95 |
| 5,429,277 * | 7/1995 | Kopp et al. ..................... 222/145.6 |
| 5,554,665 * | 9/1996 | Tatesian et al. .................. 433/90 |
| 5,631,000 * | 5/1997 | Pellico et al. .................... 424/53 |
| 5,645,428 * | 7/1997 | Yarborough et al. ............ 433/45 |
| 5,648,064 * | 7/1997 | Gaffar et al. ..................... 424/53 |
| 5,676,933 * | 10/1997 | Hauschild ......................... 424/53 |
| 5,713,738 * | 2/1998 | Yarborough ..................... 433/215 |
| 5,785,527 * | 7/1998 | Jenson et al. .................... 433/215 |
| 5,814,303 * | 9/1998 | Williams et al. ................. 424/57 |
| 5,814,681 * | 9/1998 | Hino et al. ....................... 222/145.5 |
| 5,829,639 * | 11/1998 | Horner ............................. 222/137 |
| 5,855,875 * | 1/1999 | Williams et al. ................. 424/57 |
| 5,858,332 * | 1/1999 | Jensen et al. ..................... 424/53 |
| 5,902,568 * | 5/1999 | Ryles et al. ...................... 424/53 |
| 5,922,307 * | 7/1999 | Montgomery .................... 424/53 |
| 5,928,628 * | 7/1999 | Pellico ............................. 424/49 |
| 6,017,515 * | 1/2000 | Van Den Bosch ............... 424/53 |
| 6,036,493 * | 3/2000 | Sharma ............................ 424/53 |
| 6,116,900 * | 9/2000 | Ostler .............................. 433/89 |
| 6,162,055 * | 12/2000 | Montgomery et al. ........... 433/216 |

OTHER PUBLICATIONS

Frysh et al. J Esthetic Dentistry 7(3): 130–133 Effect of pH on Hydrogen Peroxide Bleaching Agents, 1995.*

Phillips and Bowles, "Peroxide Penetration into the Dental Pulp from an Alkaline Bleaching Solution," *J. Dent. Res. 75 IADR Abstracts*), No. 2098, p. 280, 1996.*

Dentistry Today—Buyer's Guide to Whitening Systems—In Home—in Offices, Dec. 1997.*

"Mentadent" Reg.™ 1 827 994 Facsimile Specimen Label with Patents, Mar. 1994.*

Phillips and Bowles, "Peroxide Penetration into the Dental Pulp from an Alkaline Bleaching Solution," *J. Dent. Res. 75 IADR Abstracts*), No. 2098, p. 280, 1996.

* cited by examiner

*Primary Examiner*—Shep K. Rose
(74) *Attorney, Agent, or Firm*—Banner & Witcoff, Ltd.

(57) ABSTRACT

The present invention relates to improved dental compositions and methods for bleaching teeth. More specifically, this invention is directed towards hydrogen peroxide-containing compounds that are maintained at a substantially constant pH range of 6.0–10.0 during the tooth-bleaching procedure in the presence of a calcium chelating agent.

20 Claims, No Drawings

TOOTH-BLEACHING COMPOSITIONS

RELATED U.S. APPLICATION(S)

The present application is a continuation of U.S. application Ser. No. 09/054,156, filed on Apr. 2, 1998, itself a divisional of U.S. application Ser. No. 08/719,569, filed on Sep. 25, 1996, which issued on Jul. 13, 1999 as U.S. Pat. No. 5,922,307, and which claims priority from Provisional Application Serial No. 60/004,258, filed Sep. 25, 1995, all of which are hereby incorporated herein by reference.

TECHNICAL FIELD

The present invention relates to improved dental bleaching compositions and methods for bleaching teeth.

BACKGROUND ART

White teeth have long been considered cosmetically desirable. Unfortunately, teeth become almost invariably discolored in the absence of intervention. The tooth structures which are generally responsible for presenting a stained appearance are enamel, dentin, and the acquired pellicle. Tooth enamel is predominantly formed from inorganic material, mostly in the form of hydroxyapatite crystals and further contains approximately 5% organic material primarily in the form of collagen. In contrast, dentin is composed of about 20% protein including collagen, the balance consisting of inorganic material, predominantly hydroxyapatite crystals, similar to that found in enamel. The acquired pellicle is a proteinaceous layer on the surface of tooth enamel which reforms rapidly after an intensive tooth cleaning.

Staining of teeth results from extrinsic and/or intrinsic staining. Extrinsic staining of the acquired pellicle arises as a result of compounds such as tannins and polyphenolic compounds which become trapped in and tightly bound to the proteinaceous layer on the surface of the teeth. This type of staining can usually be removed by mechanical methods of tooth cleaning. In contrast, intrinsic staining occurs when staining compounds penetrate the enamel and even the dentin or arise from sources within the tooth. This type of staining is not amenable to mechanical methods of tooth cleaning and chemical methods are required.

Consequently, tooth-bleaching compositions generally fall into two categories: (1) gels, pastes, or liquids, including toothpastes that are mechanically agitated at the stained tooth surface in order to affect tooth stain removal through abrasive erosion of stained acquired pellicle; and (2) gels, pastes, or liquids that accomplish the tooth-bleaching effect by a chemical process while in contact with the stained tooth surface for a specified period, after which the formulation is removed. In some cases, the mechanical process is supplemented by an auxiliary chemical process which may be oxidative or enzymatic.

The majority of professionally-monitored at-home tooth-bleaching compositions act by oxidation. These compositions are dispensed directly to a patient for use in a custom-made tooth-bleaching tray, held in place in the mouth for contact times of greater than about 60 minutes, and sometimes as long as 8 to 12 hours. The slow rate of bleaching is in large part, the consequence of formulations that are developed to maintain stability of the oxidizing composition. The most commonly used oxidative compositions contain the hydrogen peroxide precursor carbamide peroxide which is mixed with an anhydrous or low-water content, hygroscopic viscous carrier containing glycerine and/or propylene glycol and/or polyethylene glycol. When contacted by water, carbamide peroxide dissociates into urea and hydrogen peroxide. Associated with the slow rate of bleaching in the hygroscopic carrier, the currently available tooth-bleaching compositions cause tooth sensitization in over 50% of patients. Tooth sensitivity is believed to result from the movement of fluid through the dentinal tubes toward nerve endings in the tooth. This movement is enhanced by the carriers for the carbamide peroxide. In fact, it has been determined that glycerine, propylene glycol and polyethylene glycol can each give rise to varying amounts of tooth sensitivity following exposure of the teeth to heat, cold, overly sweet substances, and other causative agents.

Prolonged exposure of teeth to bleaching compositions, as practiced at present, has a number of adverse effects in addition to that of tooth sensitivity. These include: solubilization of calcium from the enamel layer at a pH less than 5.5 with associated demineralization; penetration of the intact enamel and dentin by the bleaching agents, so as to reach the pulp chamber of a vital tooth thereby risking damage to pulpal tissue; and dilution of the bleaching compositions with saliva with resulting leaching from the dental tray and subsequent digestion.

The stability of existing formulations of hydrogen peroxide-containing tooth-bleaching compositions in terms of shelf-life as well as over the period of use in the mouth, depends, in general, on an acidic pH. The hydrogen peroxide becomes markedly less stable as the pH increases. Indeed, Frysh, et al. (Journal of Esthetic Dentistry Vol. 7, No. 3, pp. 130–133, 1995) described the use of high concentration (35%) of hydrogen peroxide solutions at an initial alkaline pH, which was required to be formulated immediately before use and was administered in the form of a liquid to extracted teeth to achieve tooth bleaching. Phillips and Bowles (IADR Abstract J. Dent.res 75, 1996) have demonstrated that hydrogen peroxide penetrates the enamel of extracted teeth less readily over a 15 minute period at pH 9.0 than at pH 4.5. Carbamide peroxide compositions have been formulated at a pH of 5.0–6.5 using hygroscopic carriers and maintaining a low water content. This type of formulation is problematic with regard to enhanced tooth sensitivity. On contact with saliva, the water content of the formulation increases, causing the carbamide to disassociate into urea and hydrogen peroxide and the pH to be decreased. In fact, the equilibrium pH of a 10% carbamide peroxide solution is approximately 3.45 and a typical commercially-available tooth-bleaching gel with 10% carbamide peroxide when combined with saliva in a 1:1 weight ratio has an initial pH of 5.6 and gradually decreases to pH 4.8 after 8 hours.

Thus, currently available tooth-bleaching compositions that rely on hydrogen peroxide as oxidizing agents, all release hydrogen peroxide from precursors at low pH levels despite the low rates of tooth-bleaching activity.

There is a need for a home use tooth-bleaching product that is stable, easy to use, and rapid-acting that utilizes reduced amounts of hydrogen peroxide and is capable of administration to a patient by means of a dental tray. There is a further need for a tooth-bleaching composition that may reduce hard and soft tissue irritation, tooth sensitivity, and bleaching composition ingestion to further increase patient compliance.

SUMMARY OF THE INVENTION

The invention satisfies the above needs. An embodiment of the invention includes a tooth-bleaching composition for contacting a tooth surface in a subject that includes a hydrogen peroxide-containing compound. Furthermore the composition includes a matrix for administering the hydrogen peroxide-containing compound to the tooth surface. The matrix comprises a thickening agent, an agent for stabilizing the hydrogen peroxide-containing compound, a pH adjusting agent and a calcium chelating agent, wherein the pH of the tooth-bleaching composition during the bleaching process is substantially constant within a range of pH 6.0–10.

A further embodiment of the invention includes a dosage delivery unit for tooth bleaching, including a multi-chamber vessel wherein each chamber is responsive to an applied pressure from an external source, such that a mixture of reagents contained within a compartment including a hydrogen peroxide containing composition and a matrix, will be forced to exit the compartment through a mixing baffle in response to the externally applied pressure.

A further embodiment of the invention includes a method for bleaching teeth including preparing a composition as described above and administering the composition to the tooth surface.

DETAILED DESCRIPTION OF THE INVENTION

The present invention comprises compositions and methods for bleaching tooth enamel in situ which allow the use of reduced concentrations of hydrogen peroxide in tooth-bleaching compositions in order to achieve effective tooth bleaching in a contact time of less than one hour.

The tooth surface is defined here and in the claims as a portion of a tooth which is directly responsible for the stained appearance of said tooth. The term tooth surface generally means a tooth's acquired pellicle, plaque, enamel, and combinations thereof.

The matrix is defined here and in the claims as the gel, paste, or liquid in which the hydrogen peroxide containing compound is placed for administration to the subject.

The subject referred to here and in the claims is commonly a human subject but also includes domestic animals.

An important aspect of the present invention is the finding that the efficiency of the bleaching reaction in a tooth using a chemical tooth-bleaching agent such as hydrogen peroxide can be significantly enhanced at a pH greater than 5.5, more particularly a pH in the range of 6–10, for example in a range of pH of 7–10, more particularly between 8.0 and 9.5, providing that the pH is maintained at a substantially constant range throughout the tooth-bleaching process and a calcium chelating agent is included in the composition to prevent precipitation of calcium ions. (Table 1–4)

Suitable pH adjusting agents include, but are not limited to, sodium hydroxide, potassium hydroxide, ammonium hydroxide, sodium carbonate, potassium carbonate, TRIS and triethanolamine.

Examples of calcium chelating agents include any of the calcium chelating agents known in the art. Examples include EDTA and its salts, citric acid and its salts, gluconic acid and its salts, alkali metal pyrophosphates and alkali metal polyphosphates. The use of citric acid, sodium acid pyrophosphate and disodium EDTA are shown in Table 1 and Table 2. The biological efficacy of sodium acid pyrophosphate is shown in Table 4. Without being bound to any particular theory, it is proposed that calcium precipitation in the form of calcium phosphates arise in the intercrystalline interstices of the tooth at elevated pHs and this gives rise to a blockage of movement of the peroxide into the tooth with a resulting negative effect on tooth bleaching. Calcium chelating agents may prevent this precipitation of calcium ions with the associated observed improvement of tooth-bleaching effect.

The composition may also contain a stabilizing agent for removing from solution, metal ions that interfere with the action of the hydrogen peroxide. In certain formulations, a single component may act either as a calcium chelating agent or as a stabilizing agent or may serve both functions.

The ability to maintain a constant pH range above 5.5 throughout the period of tooth bleaching coupled with the inhibition of calcium precipitation that normally occurs at pH levels above 5.5, has resulted in a formulation that is suitable for use in the home and is capable of achieving detectable tooth bleaching in less than 30 minutes. Furthermore, multiple treatments (each treatment lasting no longer than 30 minutes) have been demonstrated to substantially whiten teeth (Example 5). In Example 5, 14 treatments using the inventive formulation, were administered for twenty minutes, twice a day over seven days. A mean $\Delta E$ of 7.32 was observed denoting a substantial tooth-bleaching effect compared with a $\Delta E$ of 4.73 using a prior art formulation for a period of time that was three times longer than that of the novel formulation.

According to the invention, additional agents having tooth-bleaching effect may be used to achieve detectable tooth bleaching in less than 30 minutes. For example, sodium percarbonate has been demonstrated to be very effective at tooth bleaching when maintained at a pH that is greater than 5.5, more preferably in the range of 7–10, more particularly 8–9.5 that includes a calcium chelating agent. This composition differs from carbamide peroxide in that there is no acidification of that solution that results upon its dissociation. Consequently, the reagent may be maintained at a constant elevated pH for an extended period of time without the necessity for adding buffering reagents beyond that naturally supplied in the saliva. Unlike carbamide peroxide, however, the percarbonate is prepared in a formulation that does not include glycerine and is only slowly permeated by water whereupon hydrogen peroxide is released. For this reason, it may be desirable, but is not essential, to prepare the percarbonate in a two-component composition, the two components being mixed before use so as to accelerate the tooth-bleaching effect (Examples 1 and 2). Formulations containing two components may be applied to the dental tray by squeezing a tube in much the same way as a single component. The mixing of the two components can be readily achieved using a multi-component tube containing a baffle, otherwise known in the art as a static mixer such that on squeezing the tube, material from each of the compartments is forced through the static mixer and are mixed together before emerging from a single exit in the tube.

The present invention has important health benefits that follow from shorter contact times of the tooth with hydrogen peroxide as well as the need for lower concentrations of peroxide to achieve a desired tooth-bleaching effect.

EXAMPLE 1

Composition of a Stable Tooth-Bleaching Formulation Suitable for use in a One Component System.

The formulations below utilized ultrapure components to avoid destabilization caused by metal ion contaminants. The chelating agent used here is one of disodium EDTA (1C), citric acid (1B), and sodium acid pyrophosphate (1F). The pH is modified using one of sodium hydroxide monohydrate (1A, 1B, 1C), ammonium hydroxide (1F,1G), Tris (hydroxymethyl) aminomethane (1D), and triethanolamine (1E). Carbopol is a high molecular weight crosslinked polyacrylic acid thickening agent. Hydrogen peroxide is used as the oxidizing agent.

TABLE 1

| Example 1 Ingredient | A | B | C | D | E | F | G |
|---|---|---|---|---|---|---|---|
| | WEIGHT PERCENT | | | | | | |
| Distilled Water | 86.41 | 86.21 | 86.31 | 72.80 | 79.52 | 86.50 | 73.81 |
| 1-Hydroxyethylidene-1,1-diphosphonic acid | 0.02 | 0.02 | 0.02 | 0.03 | 0.02 | 0.30 | 0.40 |
| Sodium stannate trihydrate | 0.02 | 0.02 | 0.02 | 0.03 | 0.02 | 0.05 | 0.05 |
| Citric acid | — | 0.20 | — | — | — | — | 0.10 |
| Calcium disodium EDTA | — | — | 0.10 | — | — | — | — |
| Sodium acid pyrophosphate | — | — | — | — | — | 0.30 | — |
| Hydrogen Peroxide 35% | 10.30 | 10.30 | 10.30 | 17.14 | 17.14 | 8.60 | 17.14 |
| Carbopol 974P (BF Goodrich) | 2.50 | 2.50 | 2.50 | 5.00 | — | 3.00 | 5.00 |
| Carbopol 934P (BF Goodrich) | — | — | — | — | 2.00 | — | — |
| Sodium Hydroxide Monohydrate | to pH 7.0 | to pH 7.0 | to pH 7.0 | — | — | — | — |
| Ammonium hydroxide 28% | — | — | — | — | — | to pH 6.5 | to pH 8.5 |
| Tris(hydroxymethyl) aminomethane | — | — | — | to pH 8.0 | — | — | — |
| Triethanolamine | — | — | — | — | to pH 6.0 | — | — |
| Total | 100 | 100 | 100 | 100 | 100 | 100 | 100 |
| pH @ 25 deg. C. | 7.0 | 7.0 | 7.0 | 8.0 | 6.0 | 6.5 | 8.5 |

The above formulations were prepared by dissolving the stabilizers 1-hydroxyethylidene-1,1-diphosphonic acid and the sodium stannate trihydrate in the distilled water using a Kynar-coated propeller-type agitator (reserving enough water, if necessary, to dissolve the neutralizer in the final step). The hydrogen peroxide was then added slowly to this mixture. The Carbopol 974P was then added to the distilled water/stabilizer/hydrogen peroxide mixture slowly while a vortex was formed with the agitator blade. This dispersion was then placed in a Kynar-coated vacuum double planetary mixer to which the pH adjusting agent was added slowly to affect neutralization of the Carbopol 974P and to adjust the final composition pH. The resulting composition was a transparent, viscous gel and was packaged in foil/plastic laminate tubes having a polyethylene product contact liner.

EXAMPLE 2

A Two Component Alkaline Tooth-Bleaching Formulation.

A hydrogen peroxide-releasing composition was formulated which utilized sodium percarbonate in an anhydrous gel, and was designed to be combined with a separate aqueous gel prior to use in order to dissolve the sodium percarbonate to form hydrogen peroxide and sodium carbonate. The pH of this composition, shown in Table 2, when combined in a volume ratio of 1 to 1, was 9.0. The chelating agents used here are EDTA and sodium acid pyrophosphate.

TABLE 2

| EXAMPLE 2 INGREDIENT | PART A | PART B |
|---|---|---|
| | WEIGHT PERCENT | |
| Distilled Water | — | 95.20 |
| Polyethylene glycol 400 | 83.00 | — |
| Sodium percarbonate (powder) | 12.00 | — |
| EDTA | — | 0.20 |
| Sodium acid pyrophosphate | — | 0.30 |
| Carbopol 974P (B F Goodrich) | 2.50 | 4.00 |
| Sodium Hydroxide Monohydrate | — | to pH 7.0 |
| Tris(hydroxymethyl)aminomethane | 2.50 | — |
| Total | 100 | 100 |

The above composition parts were prepared as follows:
Part A—The Carbopol was dispersed in the polyethylene glycol using a propeller-type agitator with Kynar-coated product contact surfaces. The resulting dispersion was added to a Kynar-coated vacuum double planetary mixer (as in Example 1) and neutralized with the tris(hydroxymethyl) aminomethane under low shear mixing. To the resultant neutralized Carbopol gel, sodium percarbonate was added and dispersed until the composition was a homogenous white paste.

Part B—The Carbopol was added to the water (in which the EDTA and sodium acid pyrophosphate had already been dissolved) and agitated as above. The resulting dispersion was transferred to the Kynar-coated vacuum double planetary mixer and neutralized with the sodium hydroxide monohydrate under low shear mixing. The final gel was clear and viscous, with a pH of around 7.0.

Example 3

Preparation of a Tooth-Bleaching Formulation having Acidic pH

In order to demonstrate the superior ability of the inventive hydrogen peroxide gel composition of Examples 1 and 2 to bleach teeth, a composition was prepared which was similar to that of Example 1E, except that the pH was adjusted to 4.5.

TABLE 3

| INGREDIENT | PERCENT |
|---|---|
| Distilled water | 79.82 |
| 1-Hydroxyethylidene-1,1-diphosphonic acid | 0.02 |
| Sodium stannate trihydrate | 0.02 |
| Carbopol 974P | 2.00 |
| Hydrogen Peroxide 35% | 17.14 |
| Triethanolamine | 1.00 |
| TOTAL | 100.00 |

The formulation was prepared as in Example 1, resulting in a transparent, viscous gel with a pH of approximately 4.5. The formulation is similar to 1E, the difference lying in the pH of the composition.

Example 4

Assay to Determine Tooth Bleaching.

Bovine incisors, which had been imbedded in an acrylic matrix such that the buccal surfaces presented themselves on the top surface, were stained in a manner to duplicate the tooth staining observed in vivo by humans (alternately exposed to air and a staining broth at 37 degrees C. containing typticase soy broth, tea, coffee, mucin, $FeCl_3$, and *Sarcina lutea*, for a period of about four days). Each stained bovine incisor was numbered and measured for degree of staining (color by the CIELAB protocol) with a Minolta 5031 Spectrophotometer (3 mm aperture, 8 exposure averaging, outliers discarded). Incisors were covered with different tooth-bleaching compositions in the tables above, in addition to a commercially available carbamide peroxide composition (Opalescence 10% Carbamide Peroxide Gel, Ultradent, South Jordan, Utah). All gels were kept in contact with the incisor surface for exactly 15 minutes, whereupon the tooth was rinsed clean of any gel residue with distilled water and swabbed with saliva. The degree of stain removal was thereafter immediately determined by measuring the incisor surface, as above, for color, and the change in tooth color recorded below as $\Delta E$. Absolute color change is defined as the square root of the sum of the squares of all color components (L, a, and b).

$$\sqrt{(\Delta L)^2 + (\Delta a)^2 + (\Delta b)^2} = \Delta E$$

TABLE 4

| Tooth # | Product/ Example | pH (neat) | Initial Color L | a | b | Final Color L | a | b | ΔE |
|---|---|---|---|---|---|---|---|---|---|
| 1 | Opalescence | 6.5 | 41.79 | 3.17 | 11.78 | 44.29 | 2.96 | 11.70 | 2.51 |
| 2 | Example 3 | 4.5 | 39.84 | 4.99 | 12.00 | 43.96 | 4.47 | 10.94 | 4.29 |
| 3 | 1E | 6.0 | 40.44 | 4.41 | 9.53 | 46.32 | 3.48 | 7.54 | 6.27 |
| 4 | 1A | 7.0 | 36.02 | 3.84 | 10.10 | 42.57 | 2.59 | 8.28 | 6.91 |
| 5 | 1B | 7.0 | 38.81 | 3.98 | 11.38 | 45.92 | 2.38 | 8.81 | 7.73 |
| 6 | 1C | 7.0 | 36.90 | 4.05 | 12.61 | 44.11 | 2.45 | 10.53 | 7.67 |
| 7 | 1D | 8.0 | 41.55 | 3.67 | 10.51 | 49.77 | 1.26 | 7.82 | 8.98 |
| 8 | 1F | 6.5 | 38.55 | 5.01 | 10.87 | 44.78 | 3.67 | 9.50 | 6.52 |
| 9 | 1G | 8.5 | 40.26 | 4.59 | 9.93 | 48.28 | 3.13 | 7.97 | 8.38 |
| 10 | Example 2 | 9.0 | 36.49 | 4.00 | 12.64 | 44.93 | 2.20 | 10.63 | 8.78 |

This table shows the effect of pH on tooth bleaching. As shown for tooth #2 treated with the formulation of Example 3 and tooth #3 treated with the formulation of 1E in Example 1, the increase in pH from 4.5 (2) to 6.0 (3) results in an increased $\Delta E$ from 4.29 to 6.27.

The table further shows the positive effect of the calcium chelating agent on tooth bleaching. For example, for 1A, 1B, and 1C (all at pH 7.0), 1A lacked a calcium chelating agent whereas 1B and 1C contained a chelating agent. There was an observed improvement in $\Delta E$ in the presence of the chelating agent. The best tooth-bleaching results were obtained at the highest pH, namely, in this experiment, pH 8.0 and pH 9.0.

Opalescence is a commercial product which has been pH adjusted to pH 6.5 before use but shows a poor performance with regard to color change over the time of the experiment. It is proposed that the pH of the formulation is lowered as hydrogen peroxide and urea is released following dissociation of carbamide peroxide.

Example 5

In Vivo Demonstration of Tooth Bleaching

Six volunteers aged 25 to 43 were separated into two groups of two and custom dental trays were fashioned for each participant in the study.

One group was given an unmarked 2 oz. tube containing the composition of Example 1B and instructed to place a small amount of tooth-bleaching material into the tray, position the tray over the teeth, and leave the tray in place for 20 minutes. Patients were instructed to repeated this procedure twice a day for one week, for a total of 14 treatments and 280 minutes total tooth whitener exposure time.

The second group was given an unmarked 2 oz. tube of Opalescence 10% Carbamide Peroxide tooth-bleaching gel and instructed as above, with the exception of the duration of the bleaching procedure to be 60 minutes. Patients were instructed to repeat the procedure twice a day for one week, for a total of 14 treatments and 840 minutes total tooth-bleaching exposure time.

The results of direct tooth surface (upper left central incisor) color measurements, both before and after treatment (as in Example 5 above), are recorded in the Table 5 below.

TABLE 5

| Patient # | Product/ Example | Treatment Time (minutes) | Initial Color L | a | b | Final Color L | a | b | ΔE |
|---|---|---|---|---|---|---|---|---|---|
| 1 | 1B | 280 | 53.76 | 4.65 | 11.65 | 60.34 | 0.97 | 8.80 | 8.06 |
| 2 | 1B | 280 | 49.42 | 2.97 | 9.48 | 56.99 | 0.46 | 7.38 | 8.25 |
| 3 | 1B | 280 | 51.26 | 2.33 | 8.25 | 55.63 | 0.87 | 4.99 | 5.65 |
| 4 | Opalescence | 840 | 52.78 | 1.75 | 6.14 | 57.26 | 1.42 | 2.10 | 6.04 |
| 5 | Opalescence | 840 | 56.35 | 1.79 | 5.21 | 59.13 | 0.65 | 2.44 | 4.09 |
| 6 | Opalescence | 840 | 55.71 | 2.72 | 7.10 | 58.60 | 1.09 | 4.75 | 4.07 |

The average $\Delta E$ for the Example IB group was 7.32, whereas the average $\Delta E$ for the Opalescence group was 4.73. The present inventive compositions are thus shown to offer a substantially improved degree of tooth bleaching in a shorter exposure time than a prior art composition.

I claim:

1. A single exit dual compartment squeeze tube with a static mixer, whose compartments are adapted to keep apart two formulations and whose two compartments respectively include:

a first formulation comprising a hydrogen peroxide precursor compound selected from the group consisting of an alkali metal percarbonate, carbamide peroxide, calcium peroxide, and an alkali metal perborate, a thickener, a carrier and a calcium chelating agent wherein the first formulation is substantially free of an alkaline pH adjusting agent and is substantially free of water; and a second formulation comprising an alkaline pH-adjusting agent selected from the group consisting of alkali metal hydroxides, ammonium hydroxide, alkali metal carbonates, TRIS, and triethanolamine, a carrier and a thickener wherein the second formulation is substantially tree of the hydrogen peroxide precursor compound; whereby squeezing the tube forces material from each compartment through the static mixer to form a thickened, aqueous, substantially bicarbonate free, and substantially abrasive free hydrogen peroxide containing mixture before emerging from the single exit in the tube, wherein the mixture has a range of pH between approximately 6 and approximately 10.

2. The single exit dual compartment squeeze tube according to claim 1, wherein the hydrogen peroxide precursor compound is a percarbonate salt.

3. The single exit dual compartment squeeze tube according to claim 2, wherein the percarbonate salt is selected from the group consisting of sodium and potassium percarbonate.

4. The single exit dual compartment squeeze tube according to claim 1, wherein the calcium chelating agent is selected from the group consisting of EDTA and its salts, citric acid and its salts, gluconic acid and its salts, alkali metal pyrophosphates and alkali metal polyphosphates.

5. The single exit dual compartment squeeze tube according to claim 4, wherein the calcium chelating agent further acts as a stabilizing agent for the hydrogen peroxide precursor compound.

6. The single exit dual compartment squeeze tube according to claim 8, wherein the calcium chelating agent is 1-hydroxyethylidene-1,1-diphosphonic acid.

7. The single exit dual compartment squeeze tube according to claim 1, wherein the composition is capable of a detectable tooth-bleaching effect within 30 minutes.

8. The single exit dual compartment squeeze tube according to claim 1, the first formulation comprising:
less than about 0.5% by weight, based on the weight of the mixture, of the calcium chelating agent.

9. The single exit dual compartment squeeze tube according to claims 8, wherein the first formulation has less than about 0.1% by weight, based on the weight of the composition, of the calcium chelating agent.

10. The single exit dual compartment squeeze tube according to claim 1, wherein the second formulation is aqueous.

11. The single exit dual compartment squeeze tube according to claim 1, wherein the thickening agent is a high molecular weight cross linked polyacrylic acid.

12. A single exit dual compartment squeeze tube with a static mixer, whose compartments are adapted to keep apart two formulations and whose two compartments respectively include:

a first formulation comprising hydrogen peroxide, a thickener, an aqueous carrier and a chelating agent wherein the first formulation is substantially free of an alkaline pH adjusting agent; and a second formulation comprising an alkaline pH-adjusting agent selected from the group consisting of alkali metal hydroxides, ammonium hydroxide, alkali metal carbonates, TRIS, and triethanolamine, a carrier and a thickener wherein the second formulation is substantially free of the hydrogen peroxide; whereby squeezing the tube forces material from each compartment through the static mixer to form a thickened, aqueous, substantially bicarbonate free, and substantially abrasive free hydrogen peroxide containing mixture before emerging from the single exit in the tube, wherein the mixture has a range of pH between approximately 6 and approximately 10.

13. The single exit dual compartment squeeze tube according to claim 12, wherein the concentration of hydrogen peroxide in the composition is less than 15% by weight of the mixture.

14. The single exit dual compartment squeeze tube according to claim 12, wherein the calcium chelating agent is selected from the group consisting of EDTA and its salts, citric acid and its salts, gluconic acid and its salts, alkali metal pyrophosphates and alkali metal polyphosphates.

15. The single exit dual compartment squeeze tube according to claim 12, wherein the calcium chelating agent is 1-hydroxyethylidene-1,1-diphosphonic acid.

16. The single exit dual compartment squeeze tube according to claim 1, wherein the mixture is capable of a detectable tooth-bleaching effect within 30 minutes.

17. The single exit dual compartment squeeze tube according to claim 12, the first formulation comprising:
less than about 0.5% by weight, based on the weight of the mixture, of the calcium chelating agent.

18. The single exit dual compartment squeeze tube according to claim 12, wherein the first formulation has less than about 0.1% by weight, based on the weight of the composition, of the calcium chelating agent.

19. The single exit dual compartment squeeze tube according to claim 12, wherein the concentration of hydrogen peroxide in the mixture is in a range between approximately 5% and approximately 12% by weight of the mixture.

20. The single exit dual compartment squeeze tube according to claim 12, wherein the thickening agent is a high molecular weight cross linked polyacrylic acid.

* * * * *